US009808409B2

(12) United States Patent
Allard et al.

(10) Patent No.: US 9,808,409 B2
(45) Date of Patent: Nov. 7, 2017

(54) COMPOSITION COMPRISING (2,5-DIAMINOPHENYL)ETHANOL AND A CELLULOSE POLYMER OR CARBOXYLIC ANIONIC POLYMER IN A MEDIUM RICH IN FATTY SUBSTANCES, DYEING PROCESS AND DEVICE

(71) Applicant: L'OREAL, Paris (FR)

(72) Inventors: Delphine Allard, Paris (FR); Valerie Nicou, Clichy (FR); Isabelle Rollat, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/389,533

(22) PCT Filed: Mar. 27, 2013

(86) PCT No.: PCT/EP2013/056590
§ 371 (c)(1),
(2) Date: Oct. 3, 2013

(87) PCT Pub. No.: WO2013/144243
PCT Pub. Date: Oct. 3, 2013

(65) Prior Publication Data
US 2015/0335563 A1 Nov. 26, 2015

Related U.S. Application Data

(60) Provisional application No. 61/640,270, filed on Apr. 30, 2012, provisional application No. 61/700,977, filed on Sep. 14, 2012.

(30) Foreign Application Priority Data

Mar. 30, 2012 (FR) ...................... 12 52925
Mar. 30, 2012 (FR) ...................... 12 52947

(51) Int. Cl.
*A61Q 5/10* (2006.01)
*A61K 8/31* (2006.01)
*A61K 8/81* (2006.01)
*A61K 8/22* (2006.01)
*A61K 8/41* (2006.01)
*A61K 8/73* (2006.01)
*A61K 8/92* (2006.01)

(52) U.S. Cl.
CPC .............. *A61K 8/31* (2013.01); *A61K 8/22* (2013.01); *A61K 8/411* (2013.01); *A61K 8/731* (2013.01); *A61K 8/8141* (2013.01); *A61K 8/922* (2013.01); *A61Q 5/10* (2013.01); *A61K 2800/43* (2013.01); *A61K 2800/48* (2013.01); *A61K 2800/5424* (2013.01); *A61K 2800/592* (2013.01); *A61K 2800/882* (2013.01)

(58) Field of Classification Search
CPC ............ A61Q 5/10; A61K 8/22; A61K 8/411; A61K 8/731; A61K 8/8141; A61K 2800/882; A61K 2800/592; A61K 2800/5424

USPC ............................................ 8/405
See application file for complete search history.

(56) References Cited

U.S. PATENT DOCUMENTS

| 3,915,921 A | 10/1975 | Schlatzer, Jr. |
| 4,003,699 A | 1/1977 | Rose et al. |
| 4,131,576 A | 12/1978 | Iovine et al. |
| 4,137,180 A | 1/1979 | Naik et al. |
| RE30,199 E | 1/1980 | Rose et al. |
| 4,509,949 A | 4/1985 | Huang et al. |
| 4,874,554 A | 10/1989 | Lange et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 5,961,667 A | 10/1999 | Doehling et al. |

(Continued)

FOREIGN PATENT DOCUMENTS

| DE | 2359399 A1 | 6/1975 |
| DE | 3843892 A1 | 6/1990 |
| DE | 4133957 A1 | 4/1993 |
| DE | 19543988 A1 | 5/1997 |
| DE | 19724334 C1 | 8/1998 |
| DE | 19828204 C1 | 10/1999 |
| EP | 0173109 A2 | 3/1986 |
| EP | 0216479 A1 | 4/1987 |
| EP | 0727203 A1 | 8/1996 |
| EP | 0770375 A1 | 5/1997 |
| EP | 0858796 A2 | 8/1998 |
| EP | 0985406 A1 | 3/2000 |
| EP | 2103299 A2 | 9/2009 |
| FR | 2733749 A1 | 11/1996 |
| FR | 2801308 A1 | 5/2001 |
| GB | 1026978 A | 4/1966 |

(Continued)

OTHER PUBLICATIONS

Todd, Charles, et al., "Volatile Silicone Fluids for Cosmetic Formulations," Cosmetics and Toiletries, vol. 91, Jan. 1976, pp. 29-32.

(Continued)

*Primary Examiner* — Eisa Elhilo
(74) *Attorney, Agent, or Firm* — The Marbury Law Group, PLLC

(57) ABSTRACT

The present invention relates to a composition for dyeing keratin fibers, comprising a) one or more fatty substances, which are preferably liquid and non-silicone, b) one or more cellulose polymers and/or one or more carboxylic anionic, c) (2,5-diaminophenyl)ethanol, d) optionally, one or more couplers, e) optionally, one or more basifying agents, and f) one or more chemical oxidizing agents such as hydrogen peroxide, and the content of fatty substances in the composition representing in total at least 10%, in particular at least 15%, more particularly at least 20% and preferably at least 25% by weight relative to the total weight of the composition resulting from the mixing of (A')+(B')+(C'). The present invention also relates to a process using this composition and to a multi-compartment device suitable for the use of said process.

25 Claims, No Drawings

(56) References Cited

U.S. PATENT DOCUMENTS

| | | |
|---|---|---|
| 6,099,592 A | 8/2000 | Vidal et al. |
| 6,102,974 A | 8/2000 | Braun |
| 6,224,637 B1 | 5/2001 | Golinski et al. |
| 6,284,003 B1 | 9/2001 | Rose et al. |
| 6,338,741 B1 | 1/2002 | Vidal et al. |
| 6,503,282 B1 | 1/2003 | Braun |
| 6,645,258 B2 | 11/2003 | Vidal et al. |
| 6,730,789 B1 | 5/2004 | Birault et al. |
| 2002/0050013 A1 | 5/2002 | Vidal et al. |
| 2003/0019051 A9 | 1/2003 | Vidal et al. |
| 2010/0154140 A1* | 6/2010 | Simonet .................. A61K 8/31  8/416 |

FOREIGN PATENT DOCUMENTS

| | | |
|---|---|---|
| GB | 1153196 A | 5/1969 |
| JP | 02-19576 | 1/1990 |
| JP | 05-163124 | 6/1993 |
| WO | 94/08969 A1 | 4/1994 |
| WO | 94/08970 A1 | 4/1994 |
| WO | 96/15765 A1 | 5/1996 |
| WO | 98/17233 A1 | 4/1998 |
| WO | 98/19658 A1 | 5/1998 |
| WO | 98/19659 A1 | 5/1998 |
| WO | 98/19660 A1 | 5/1998 |
| WO | 01/51019 A1 | 7/2001 |

OTHER PUBLICATIONS

Porter, M.R., "Handbook of Surfactants," Blackie, Glasgow and London, 1991, pp. 116-178.
English language abstract for DE 19724334, (1998).
English language abstract for DE19828204, (1999).
English language abstract for EP 0727203, (1996).
English language abstract for EP 0770375, (1997).
English language abstract for JP 02-019576, (1990).
English language abstract for JP 05-163124, (1993).

* cited by examiner

COMPOSITION COMPRISING (2,5-DIAMINOPHENYL)ETHANOL AND A CELLULOSE POLYMER OR CARBOXYLIC ANIONIC POLYMER IN A MEDIUM RICH IN FATTY SUBSTANCES, DYEING PROCESS AND DEVICE

This is a national stage application of PCT/EP2013/056590, filed internationally on Mar. 27, 2013, which claims priority to U.S. Provisional Application No. 61/640,270, filed on Apr. 30, 2012, and U.S. Provisional Application No. 61/700,977, filed on Sep. 14, 2012, as well as French Application Nos. 1252925 and 1252947, both filed Mar. 30, 2012, all of which are incorporated herein by reference in their entireties.

The present invention relates to a composition for dyeing keratin fibres, comprising a) one or more fatty substances, which are preferably liquid and non-silicone, b) one or more cellulose polymers and/or one or more carboxylic anionic, and preferably acrylic, polymers, c) (2,5-diaminophenyl)ethanol and also acid salts thereof or solvates thereof, d) optionally, one or more couplers, e) optionally, one or more basifying agents, and f) one or more chemical oxidizing agents such as hydrogen peroxide, and the content of fatty substances in the composition representing in total at least 10%, in particular at least 15%, more particularly at least 20% and preferably at least 25% by weight relative to the total weight of the composition.

The present invention also relates to a dyeing process using this composition, and to a multi-compartment device that is suitable for the use of this composition.

Many people have sought for a long time to modify the colour of their hair and in particular to mask their grey hair.

One of the dyeing methods is "permanent" or oxidation dyeing, which uses dyeing compositions containing oxidation dye precursors, generally known as oxidation bases. These oxidation bases are colourless or weakly coloured compounds which, in combination with oxidizing products, can give rise to coloured compounds by an oxidative condensation process.

It is also known that the shades obtained with these oxidation bases may be varied by combining them with couplers or colouration modifiers, the latter being chosen especially from aromatic meta-diamines, meta-aminophenols, meta-diphenols and certain heterocyclic compounds such as indole compounds. The variety of the molecules used as oxidation bases and couplers allows a rich palette of colours to be obtained.

It is also possible to use direct dyes in order especially to contribute glints to the colouration obtained. These direct dyes are coloured and colouring molecules that have an affinity for the fibres. Examples that may be mentioned include nitrobenzene, anthraquinone, nitropyridine, azo, xanthene, acridine, azine and triarylmethane direct dyes.

Permanent dyeing processes thus consist in using, with the dye composition, an aqueous composition comprising at least one oxidizing agent, under alkaline pH conditions in the vast majority of cases. The role of this oxidizing agent is, at least partly, to degrade the melanin of the hair, which, depending on the nature of the oxidizing agent present, leads to more or less pronounced lightening of the fibres. The oxidizing agent used is generally hydrogen peroxide.

One of the difficulties encountered during the implementation of the dyeing processes of the prior art arises from the fact that they are carried out under alkaline conditions and that the basifying agents most commonly used are aqueous ammonia and amines. Specifically, the basifying agent makes it possible to adjust the pH of the composition to an alkaline pH to enable activation of the oxidizing agent. In addition, this basifying agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

However, these basifying agents, and especially aqueous ammonia, cause the user discomfort due to their strong characteristic odour.

Moreover, the user may not only be inconvenienced by the odour, but may also be confronted with greater risks of intolerance, for instance irritation of the scalp, which is especially reflected by stinging.

It is also important to obtain colourations that are light-fast. However, the use of certain couplers such as meta-phenylenediamines, for example, induces degradation caused by sunlight.

Moreover, it has been proposed in oxidation dyeing to use an oxidation base of (2,5-diaminophenyl)ethanol type (EP 0 858 796). Colourations that use this oxidation base are also known, especially combined with particular acids such as diethylenetriaminepenta(methylene)phosphonic acid (EP 2 103 299) or with chlorinated bases or chlorinated couplers such as 2-amino-6-chloro-4-nitrophenol, 2,6-dichloro-4-aminophenol, 2-chloro-6-ethylamino-4-nitrophenol 3-amino-5-chloroaniline, 2-chloro-4-aminophenol or 2-chloro-6-methyl-3-aminophenol (WO 98/17233, WO 98/19658, WO 98/19659, WO 98/19660, EP 0 985 406, EP 0 727 203, DE 19828204, DE 19724334 or WO 96/15765), or with couplers such as 3-(2,4-diaminophenoxy)-1-propanol (WO 2001/051019). However, these combinations of bases, couplers and acids produce colours that are not always satisfactory, whose dyeing power is limited or even insufficient to ensure in particular suitable coverage of grey hair and/or which show excessive selectivity of the colouration between the root and the end and/or insufficient fastness with respect to external attacking factors such as light, shampoos, inclement weather, etc. In addition, none of these documents describes a dye composition comprising a large amount of fatty substances, in particular of oil.

One of the objectives of the present invention is to propose compositions for dyeing human keratin fibres such as the hair that do not have the drawbacks of existing compositions.

In particular, the composition according to the invention in the presence of a chemical oxidizing agent makes it possible to obtain colours that are satisfactory, especially in terms of power in general, but also with satisfactory coverage or build-up of the colour at the root of the hair, which makes it possible to avoid a "root" effect of the colouration. The colourations obtained are also sparingly selective. Finally, it is also possible to obtain colours that are very light-fast.

Furthermore, the invention makes it possible to achieve substantial degrees of lightening while at the same time colouring, without using persalts or increasing the amount of chemical oxidizing agent or of basifying agent.

These aims and others are achieved by the present invention, one subject of which is thus a cosmetic composition for dyeing keratin fibres, in particular human keratin fibres such as the hair, comprising:
  a) one or more fatty substances, which are preferably liquid and non-silicone;

b) one or more cellulose polymer(s) and/or one or more carboxylic anionic polymer(s); preferentially one or more cellulose polymer(s) or one or more carboxylic anionic polymer(s);

c) one or more oxidation base(s) chosen from (2,5-diaminophenyl)ethanol and also acid salts thereof or solvates thereof such as hydrates;

d) optionally one or more coupler(s);

e) optionally one or more basifying agent(s);

f) one or more chemical oxidizing agent(s); and the fatty substance content representing in total at least 10%, in particular at least 15%, more particularly at least 20% and preferably at least 25% even more particularly at least 30%, more preferentially at least 40% and even more preferentially at least 50% by weight relative to the total weight of the composition.

A subject of the present invention is also processes for dyeing keratin fibres, in particular human keratin fibres such as the hair, using the composition of the invention.

The invention also relates to a multi-compartment device for using the composition of the invention.

Thus, the use of the dyeing composition according to the invention on keratin fibres leads to powerful, intense, chromatic and/or sparingly selective colourations, i.e. colourations that are uniform along the fibre.

The dyeing process of the invention also makes it possible to cover keratin fibres particularly well at their root, especially down to three centimeters from the base of said fibres. Moreover, the colours obtained after treating the fibres remain stable, in particular with respect to light.

The invention also makes it possible to reduce the amounts of active agents of the invention such as the dyes and/or basifying agents and/or oxidizing agents.

Furthermore, the processes according to the invention use formulations that are less malodorous during their application to the hair or during their preparation.

Other characteristics and advantages of the invention will emerge more clearly on reading the description and the examples that follow.

In the text hereinbelow, and unless otherwise indicated, the limits of a range of values are included in that range.

The human keratin fibres treated via the process according to the invention are preferably the hair.

The expression "at least one" is equivalent to the expression "one or more".

a) Fatty Substances

As has been mentioned, the composition of the invention comprises a) one or more fatty substances.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They exhibit, in their structure, at least one hydrocarbon-based chain comprising at least 6 carbon atoms or a sequence of at least two siloxane groups. In addition, fatty substances are generally soluble in organic solvents under the same temperature and pressure conditions, such as, for example, chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (—C(O)OH or —C(O)O−). In particular, the fatty substances of the invention are neither polyoxyalkylenated nor polyglycerolated.

Preferably, the fatty substances used in the composition according to the invention are non-silicone oils.

The term "oil" means a "fatty substance" that is liquid at ambient temperature (25° C.) and at atmospheric pressure (760 mmHg).

The term "non-silicone oil" means an oil not containing any silicon atoms (Si) and the term "silicone oil" means an oil containing at least one silicon atom.

In other words, the fatty substance(s) are preferably non-silicone liquid fatty substances.

More particularly, the fatty substances are chosen from $C_6$-$C_{16}$ hydrocarbons, hydrocarbons containing more than 16 carbon atoms, non-silicone oils of animal origin, vegetable oils of triglyceride type, synthetic triglycerides, fluoro oils, fatty alcohols other than b) the fatty alcohol(s) comprising at least 20 carbon atoms as defined below, esters of fatty acids and/or of fatty alcohols other than triglycerides, and plant waxes, non-silicone waxes and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, optionally substituted, in particular, with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of vegetable or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and shea butter oil.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition according to the invention are saturated or unsaturated, and linear or branched, and comprise from 6 to 30 carbon atoms and more particularly from 8 to 18 carbon atoms. Mention may be made, for example, of cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol.

The wax(es) that may be used in the composition according to the invention are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the esters of fatty acids and/or of fatty alcohols, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds which have several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant can also be chosen from mono-, di-, tri- and tetraesters, polyesters, and mixtures thereof.

These esters can, for example, be oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name Ryoto Sugar Esters, for example referenced B370 and corresponding to sucrose behenate formed from 20% monoester and 80% diester, triester and polyester;
  the sucrose monopalmitate/stearate-dipalmitate/stearate sold by Goldschmidt under the name Tegosoft® PSE.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's *Chemistry and Technology of Silicones* (1968), Academic Press. They can be volatile or non-volatile.

When they are volatile, the silicones are more particularly chosen from those having a boiling point of between 60° C. and 260° C., and more particularly still from:
  (i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula (A1) below:

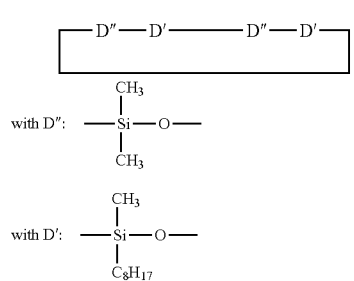

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones coming within this category are also described in the paper published in Cosmetics and Toiletries, Vol. 91, January 76, P. 27-32—TODD & BYERS "Volatile Silicone fluids for cosmetics".

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without implied limitation, of the following commercial products:
- the Silbione® oils of the 47 and 70 047 series or the Mirasil® oils sold by Rhodia, such as, for example, the oil 70 047 V 500 000;
- the oils of the Mirasil® series sold by Rhodia;
- the oils of the 200 series from the company Dow Corning, such as DC200 with a viscosity of 60 000 mm²/s;
- the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;
- the mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;
- the mixtures of two PDMSs with different viscosities, and more particularly of a PDMS gum and a PDMS oil, such as the product SF 1236 from General Electric. The product SF 1236 is a mixture of a gum SE 30 defined above, with a viscosity of 20 m²/s, and of an oil SF 96 with a viscosity of $5 \times 10^{-6}$ m²/s. This product preferably comprises 15% of gum SE 30 and 85% of an oil SF 96.

The organopolysiloxane resins that can be used in accordance with the invention are crosslinked siloxane systems containing the following units:

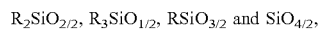

in which R represents an alkyl containing 1 to 16 carbon atoms. Among these products, those that are particularly preferred are those in which R denotes a $C_1$-$C_4$ lower alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones that can be used in accordance with the invention are silicones as defined above and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Among these polyalkylarylsiloxanes, examples that may be mentioned include the products sold under the following names:
- Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Mention may also be made, among the organomodified silicones, of polyorganosiloxanes comprising:

substituted or unsubstituted amino groups, such as the products sold under the names GP 4 Silicone Fluid and GP 7100 by Genesee or the products sold under the names Q2 8220 and Dow Corning 929 or 939 by the company Dow Corning. The substituted amino groups are, in particular, $C_1$-$C_4$ aminoalkyl groups;

alkoxylated groups, such as the product sold under the name Silicone Copolymer F-755 by SWS Silicones, and Abil Wax® 2428, 2434 and 2440 by Goldschmidt.

Preferably, the fatty substances according to the invention are non-silicone.

More particularly, the fatty substances are chosen from compounds that are liquid or pasty at ambient temperature (25° C.) and at atmospheric pressure.

Preferably, the fatty substance is a compound that is liquid at the temperature of 25° C. and at atmospheric pressure.

Even more preferentially, the fatty substances used in the dye composition according to the invention are liquid and non-silicone.

The fatty substances are advantageously chosen from $C_6$-$C_{16}$ hydrocarbons, hydrocarbons containing more than 16 carbon atoms, triglycerides, fatty alcohols, esters of fatty acids and/or of fatty alcohols other than triglycerides, or mixtures thereof.

Preferably, the fatty substance(s) is (are) chosen from liquid petroleum jelly, polydecenes, liquid fatty alcohols and liquid esters of fatty acids and/or of fatty alcohols, or mixtures thereof.

Even more preferentially, the fatty substances are chosen from liquid petroleum jelly and octyldodecanol.

The composition according to the invention comprises at least 10%, in particular at least 15%, more particularly at least 20% and preferably at least 25%, even more particularly at least 30%, more preferably at least 40% and even more preferably at least 50% by weight of fatty substances, which are preferably non-silicone, in particular of oils, preferably non-silicone oils, relative to the total weight of the composition.

The composition according to the invention more particularly has a content of fatty substances, which are preferably non-silicone, in particular of oils, preferably non-silicone oils, ranging from 10% to 80%, more preferentially from 15% to 80% by weight, preferably from 25% to 75% by weight, better still from 30% to 70% by weight and even more advantageously from 30% to 60% by weight relative to the weight of the composition.

b) Cellulose Polymer(s) and/or Carboxylic Anionic Polymer(s)

According to one particular embodiment of the invention, the ingredient b) represents one or more thickening cellulose polymers.

The cellulose polymers may be associative or non-associative, anionic, cationic, amphoteric or non-ionic polymers. They may be thickeners for aqueous or oily phases.

The term "cellulose" polymer means, according to the invention, any polysaccharide compound having in its structure sequences of glucose residues linked together via β-1,4 linkages; in addition to unsubstituted celluloses, the cellulose derivatives may be anionic, cationic, amphoteric or non-ionic. Thus, the cellulose polymers of the invention can be chosen from unsubstituted celluloses, including in a microcrystalline form, and cellulose ethers. Among these cellulose polymers, cellulose ethers, cellulose esters and cellulose ester ethers are distinguished. Among the cellulose esters are inorganic esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/inorganic esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

The term "associative polymers" means polymers that are capable, in an aqueous medium, of reversibly combining with each other or with other molecules. Their chemical structure more particularly comprises at least one hydrophilic region and at least one hydrophobic region, preferably one or more hydrophobic hydrocarbon-based side chains.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms. Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

According to one particular embodiment of the invention, the cellulose polymer(s) are non-associative.

The "non-associative" cellulose polymers of the invention are cellulose polymers which do not comprise a fatty chain, i.e. which preferably do not comprise a $C_{10}$-$C_{30}$ chain in their structure.

According to a first variant, the non-associative cellulose polymer(s) are non-ionic. Mention may be made of non-ionic cellulose ethers without a $C_{10}$-$C_{30}$ fatty chain, i.e. which are "non-associative"; mention may be made of ($C_1$-$C_4$)alkylcelluloses such as methylcelluloses and ethylcelluloses (for example Ethocel standard 100 Premium from Dow Chemical); (poly)hydroxy($C_1$-$C_4$)alkylcelluloses such as hydroxymethylcelluloses, hydroxyethylcelluloses (for example Natrosol 250 HHR provided by Aqualon) and hydroxypropylcelluloses (for example Klucel EF from Aqualon); mixed (poly)hydroxy($C_1$-$C_4$)alkyl-($C_1$-$C_4$)alkylcelluloses such as hydroxypropylmethylcelluloses (for example Methocel E4M from Dow Chemical), hydroxyéthylmethylcelluloses, hydroxyéthylethylcelluloses (for example Bermocoll E 481 FQ from Akzo Noble) and hydroxybutyl methylcelluloses.

According to a second variant, the non-associative cellulose polymer(s) are anionic. Among the anionic cellulose ethers without a fatty chain, mention may be made of (poly)carboxy($C_1$-$C_4$)alkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

According to a third variant, the non-associative cellulose polymer(s) are cationic. Among the cationic cellulose ethers without a fatty chain, mention may be made of cationic cellulose derivatives such as cellulose copolymers or cellulose derivatives grafted with a water-soluble quaternary ammonium monomer, and described in particular in U.S. Pat. No. 4,131,576, such as (poly)hydroxy($C_1$-$C_4$)alkyl celluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

According to another particular embodiment of the invention, the cellulose polymer(s) are associative.

Mention may in particular be made of quaternized (poly)hydroxyethylcelluloses modified with groups comprising at least one fatty chain, such as alkyl, arylalkyl or alkylaryl groups comprising at least 8 carbon atoms, or mixtures thereof. The alkyl radicals borne by the quaternized celluloses or hydroxyethylcelluloses above preferably comprise from 8 to 30 carbon atoms. The aryl radicals preferably denote phenyl, benzyl, naphthyl or anthryl groups. Mention may be made, as examples of quaternized alkylhydroxyethylcelluloses comprising $C_8$-$C_{30}$ fatty chains, of the products Quatrisoft LM 200®, Quatrisoft LM-X 529-18-A®, Quatrisoft LM-X 529-18-B® ($C_{12}$ alkyl) and Quatrisoft LM-X 529-8® ($C_{18}$ alkyl) sold by the company Aqualon, the products Crodacel QM®, Crodacel QL® ($C_{12}$ alkyl) and Crodacel QS® ($C_{18}$ alkyl) sold by the company Croda and the product Softcat SL 100® sold by the company Aqualon.

Mention may also be made of celluloses or derivatives thereof, modified with groups comprising at least one fatty chain, such as alkyl, arylalkyl or alkylaryl groups or mixtures thereof in which the alkyl groups are of $C_8$, and in particular:

non-ionic alkylhydroxyethylcelluloses such as the products Natrosol Plus Grade 330 CS and Polysurf 67 ($C_{16}$ alkyl) sold by the company Aqualon;

non-ionic nonoxynylhydroxyethylcelluloses such as the product Amercell HM-1500 sold by the company Amerchol;

non-ionic alkylcelluloses such as the product Bermocoll EHM 100 sold by the company Berol Nobel.

Among the fatty-phase thickening polymers, polymers bearing in the backbone at least one crystallizable block are preferred.

Semi-crystalline cellulose polymers can thus be used as fatty-phase thickening cellulose polymers. The semi-crystalline polymers that may be used in the context of the invention may be non-crosslinked or partially crosslinked, provided that the degree of crosslinking does not impede their dissolution or dispersion in the liquid oily phase by heating above their melting point. It may then be a case of chemical crosslinking, by reaction with a polyfunctional monomer during the polymerization. It may also be a case of physical crosslinking, which may then be due either to the establishment of bonds of hydrogen or dipolar type between groups borne by the polymer, for instance dipolar interactions between carboxylate ionomers, these interactions being in small amount and borne by the polymer backbone; or due to a phase separation between the crystallizable blocks and the amorphous blocks borne by the polymer.

Preferably, the semi-crystalline polymers that are suitable for the invention are non-crosslinked.

According to one particular embodiment of the invention, the cellulose polymer(s) are in particular mono- or polyalkylesters of cellulose and of fatty acid(s) and which in particular correspond to formula (A2) below:

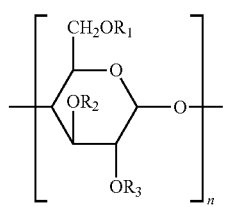

(A2)

in which formula (A2):

n is an integer ranging from 3 to 200, especially ranging from 20 to 150 and in particular ranging from 25 to 50, $R_1$, $R_2$ and $R_3$, which may be identical or different, are chosen from hydrogen and an acyl group (R—C(O)—) in which the R radical is a linear or branched, saturated or unsaturated hydrocarbon-based group containing from 7 to 29, in particular from 7 to 21, especially from 11 to 19, more particularly from 13 to 17, or even 15, carbon atoms, with the proviso that at least one of said radicals $R_1$, $R_2$ or $R_3$ is other than hydrogen.

In particular, $R_1$, $R_2$ and $R_3$ may represent hydrogen or an acyl group (R—C(O)—) in which R is a hydrocarbon-based radical as defined above, with the proviso that at least two of said radicals $R_1$, $R_2$ and $R_3$ are identical and other than hydrogen.

The radicals $R_1$, $R_2$ and $R_3$ may all represent an acyl group (R—C(O)), which may be identical or different, and especially identical.

In particular, n mentioned above advantageously ranges from 25 to 50 and is especially equal to 38 in the general formula of the saccharide ester that may be used in the present invention.

In particular, when the radicals $R_1$, $R_2$ and/or $R_3$, which may be identical or different, represent an acyl group (R—C(O)), these radicals may be chosen from caprylic, capric, lauric, myristic, palmitic, stearic, arachic, behenic, isobutyric, isovaleric, 2-ethylbutyric, ethylmethylacetic, isoheptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

The aqueous-phase or fatty-phase thickening polymers may be used alone or as mixtures in all proportions. Preferably, the thickeners are aqueous-phase thickeners. Preferably, the polymers in the cellulose compositions in accordance with the present invention advantageously have, in solution or in dispersion at 1% of active material in water, a viscosity, measured using a rheometer at 25° C., of greater than 0.1 ps and even more advantageously greater than 0.2 cp, at a shear rate of 200 s$^{-1}$.

Preferably, the cellulose polymer(s) of the invention are chosen from cellulose ethers, in particular hydroxyalkylcelluloses, in particular hydroxy($C_1$-$C_6$)alkylcelluloses, and in particular hydroxymethylcelluloses, hydroxyethylcelluloses and hydroxypropylcelluloses.

The hydroxyalkylcelluloses may be non-ionic, cationic or anionic. They are preferably non-ionic or catatonic. The hydroxyalkylceluloses of the invention are preferably hydroxyethylcelluloses and more preferentially non-ionic hydroxyethylcelluloses.

Use will even more preferentially be made of non-ionic hydroxyethylcelluloses without fatty chains or cetylhydroxyethylcelluloses, for instance the compounds sold under the names Polysurf 67CS®, Natrosol 250MR®, Natrosol 250HHR® and Natrosol Plus 330® by the company Ashland, and mixtures thereof.

The cellulose polymer(s) of the invention may be present in the dye composition of the invention in contents ranging from 0.05% to 10% by weight, in particular from 0.1% to 5% by weight and even better still from 0.5% to 2% by weight relative to the total weight of the composition.

According to another particular embodiment of the invention, the ingredient b) represents one or more carboxylic anionic polymers.

These polymers are anionic and comprise, as monomers, at least one salified or unsalified unsaturated carboxylic acid. The unsaturated carboxylic acids that may be used in the polymers of the invention are preferably chosen from the group of acrylic acid, methacrylic acid, crotonic acid, itconic acid and maleic acid.

Even more preferentially, the unsaturated carboxylic acids that may be used in the polymers of the invention are chosen from the group of acrylic acid and methacrylic acid. The corresponding anionic polymers are then called acrylic anionic polymers.

The acrylic anionic polymer(s) may be associative or non-associative.

The term "associative polymer" means, for the purposes of the present invention, any amphiphilic polymer comprising at least one $C_8$-$C_{30}$ fatty chain, that is to say therefore a hydrophobic part, and at least one hydrophilic part.

The hydrophobic part may be reduced in number with respect to the rest of the polymer chain, and may be located laterally to the chain and be distributed randomly (random copolymers) or distributed in the form of blocks or grafts (block copolymers).

Water-soluble or water-dispersible polymers can be used. Preferably, the amphiphilic polymers that are of use according to the invention are not crosslinked.

The expression "fatty chain" should be understood to mean, according to the invention, a linear or branched hydrocarbon-based group containing from 8 to 30 carbon atoms.

Among the carboxylic anionic associative polymers according to the invention, mention may be made of:
(A) copolymers comprising at least one hydrophilic unit, and at least one fatty-chain allyl ether unit, the hydrophilic unit of which is formed by a vinylcarboxylic acid and most particularly by an acrylic acid or a methacrylic acid or mixtures thereof, and the fatty-chain allyl ether unit of which corresponds to the monomer of formula (AI) below:

$H_2C=C(R')-CH_2-O-(B)_n-R$     (AI)

in which formula (AI):
R' denotes H or a ($C_1$-$C_6$)alkyl group such as $CH_3$;
B denotes the divalent radical -(alk-O)— with alk representing a linear or branched ($C_1$-$C_6$)alkylene group, such as ethyleneoxy —$CH_2$—$CH_2$—O—;
n is zero or denotes an integer ranging from 1 to 100;
R denotes a hydrocarbon-based radical chosen from alkyl, arylalkyl, aryl, alkylaryl, cycloalkyl, cycloalkylalkyl or alkylcycloalkyl radicals comprising in total from 8 to 30 carbon atoms, preferably 10 to 24, and even more particularly from 12 to 18 carbon atoms. The aryle group is preferably an aromatic monocyclic or polycyclic $C_6$-$C_{14}$ group, such as phenyle; the cycloalkyl group is a saturated hydrocarbon-based cyclic group comprising from 5 to 14 carbon atoms, such as cyclohexyl.

A unit of formula (AI) that is more particularly preferred is a unit in which R' denotes H, n is equal to 10, and R denotes a stearyl radical ($C_{18}$).

Anionic associative polymers of this type are described and prepared, according to an emulsion polymerization process, in patent EP-0 216 479.

Among these polymers, those that are particularly preferred according to the invention are polymers formed from 20% to 60% by weight of acrylic acid and/or of methacrylic acid, from 5% to 60% by weight of lower alkyl(meth)acrylates, from 2% to 50% by weight of fatty-chain allyl ether of formula (AI), and from 0 to 1% by weight of a crosslinking agent which is a well-known copolymerizable unsaturated polyethylenic monomer, for instance diallyl phthalate, allyl(meth)acrylate, divinylbenzene, (poly)ethylene glycol dimethacrylate or methylenebisacrylamide.

Among the latter polymers, the ones that are most particularly preferred are the crosslinked terpolymers sold by the company Allied Colloids under the names Salcare SC 80® and Salcare SC 90®, which are aqueous emulsions containing 30% of a crosslinked terpolymer of methacrylic acid, of ethyl acrylate and of stereath-10 allyl ether (40/50/10);

(B) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies;

(C) acrylic terpolymers comprising:
about 20% to 70% by weight of an α,β-monoethylenically unsaturated carboxylic acid,
about 20% to 80% by weight of a non-surfactant α,β-monoethylenically unsaturated monomer other than (a),
about 0.5% to 60% by weight of a non-ionic monourethane which is the product of reaction of a monohydric surfactant with a monoethylenically unsaturated monoisocyanate,
such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion (provided under the name Viscophobe DB 1000 by Amerchol);

(D) copolymers comprising among their monomers an α,β-monoethylenically unsaturated carboxylic acid and an ester of an α,β-monoethylenically unsaturated carboxylic acid and of an oxyalkylenated fatty alcohol.

Mention may be made, as compounds of this type, of Aculyn 88 and Aculyn 22 from Rohm and Haas, comprising an oxyethylenated (20 EO) stearyl methacrylate.

Preferentially, these compounds also comprise as monomer an ester of an α,β-monoethylenically unsaturated carboxylic acid and of a $C_1$-$C_4$ alcohol.

Mention may also be made, in this family, of terpolymers of methacrylic acid/alkyl acrylate/lauryl acrylate which is polyoxyethylenated, such as the product Rheo 2000 sold by Coatex, terpolymers of methacrylic acid/ethyl acrylate/behenyl methacrylate which is oxyethylenated (25 EO) provided under the name Aculyn 28 by the company Rohm and Haas, and the copolymers of acrylic acid/monostearyl itaconate which is oxyethylenated (20 EO), provided under the name Structure 2001 by the company National starch;

copolymers of methacrylic acid/alkyl acrylate/nonylphenol acrylate which is polyoxyethylenated, such as the product Rheo 3000 sold by Coatex;
(E) copolymers comprising at least one hydrophilic unit of unsaturated olefinic carboxylic acid type and at least one hydrophobic unit of $C_{10}$-$C_{30}$ alkyl ester of unsaturated carboxylic acid type.

These polymers are preferably chosen from those in which the hydrophilic unit of unsaturated olefinic carboxylic acid type corresponds to the monomer having the formula below:

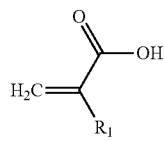

in which formula $R_1$ denotes H, $CH_3$, or $C_2H_5$, i.e. acrylic acid, methacrylic acid or ethacrylic acid units, and in which the hydrophobic unit of ($C_{10}$-$C_{30}$)alkyl ester of unsaturated carboxylic acid type corresponds to the monomer having the formula below:

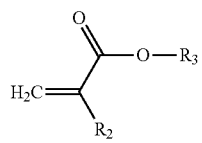

in which formula:
  $R_2$ denotes H, $CH_3$ or $C_2H_5$, i.e. acrylate, methacrylate or ethacrylate units, and preferably H (acrylate units) or $CH_3$ (methacrylate units);
  $R_3$ denoting a $C_{10}$-$C_{30}$ and preferably $C_{12}$-$C_{22}$ alkyl radical.

($C_{10}$-$C_{30}$)alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. No. 3,915,921 and U.S. Pat. No. 4,509,949.

Among anionic associative polymers of this type that will be used more particularly are polymers formed from a monomer mixture comprising:
  (i) acrylic acid;
  (ii) an ester of formula described above and in which $R_2$ denotes H or $CH_3$, $R_3$ denoting an alkyl radical containing from 12 to 22 carbon atoms;
  (iii) and a crosslinking agent, which is a well-known copolymerizable polyethylenic unsaturated monomer, such as diallyl phthalate, allyl(meth)acrylate, divinylbenzene, (poly)ethylene glycol dimethacrylate or methylenebisacrylamide.

Among anionic associative polymers of this type, use will more particularly be made of those constituted of from 95% to 60% by weight of acrylic acid (hydrophilic unit), from 4% to 40% by weight of $C_{10}$-$C_{30}$ alkyl acrylate (hydrophobic unit) and from 0% to 6% by weight of crosslinking polymerizable monomer, or alternatively those constituted of from 98% to 96% by weight of acrylic acid (hydrophilic unit), from 1% to 4% by weight of $C_{10}$-$C_{30}$ alkyl acrylate (hydrophobic unit) and from 0.1% to 0.6% by weight of crosslinking polymerizable monomer such as those described previously.

Among the above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Depending on their nature, the associative polymers according to the invention can be used in the form of aqueous solutions or in the form of aqueous dispersions.

These polymers may also be used in salified form.

For the purposes of the present invention, the term "non-associative polymer" means a polymer not simultaneously comprising at least one $C_8$-$C_{30}$ fatty chain and at least one hydrophilic unit.

The non-associative acrylic anionic polymers may be chosen from:

Acrylic or methacrylic acid homopolymers or copolymers which are optionally crosslinked and optionally salified. Mention may be made, among crosslinked copolymers of (meth)acrylic acid and of $C_1$-$C_6$ alkyl acrylate, of the product sold under the name Viscoatex 538C by the company Coatex, which is a crosslinked copolymer of methacrylic acid and of ethyl acrylate as an aqueous dispersion containing 38% active material, or the product sold under the name Aculyn 33 by the company Rohm & Haas, which is a crosslinked copolymer of acrylic acid and of ethyl acrylate as an aqueous dispersion containing 28% active material.

Mention may be made more particularly of the crosslinked methacrylic acid/ethyl acrylate copolymer in the form of an aqueous 30% dispersion manufactured and sold under the name Carbopol Aqua SF-1 by the company Noveon.

Among the acrylic acid homopolymers, mention may be made of those of the Carbopol family, including in particular Carbopol 980 (homopolymer of acrylic acid crosslinked with a pentaerythritol allyl ether, a sucrose allyl ether or a propylene allyl ether).

Among the crosslinked acrylic acid homopolymers, mention may also be made, for example, of the products sold under the names Carbopol 981, 954, 2984 and 5984 by the company Goodrich or the products sold under the names Synthalen M and Synthalen K by the company 3 VSA.

Preferably, the carboxylic anionic polymer(s) present in the dye composition are non-associative.

More preferentially, the carboxylic anionic polymer(s) present in the dye composition are chosen from acrylic acid homopolymers which are preferably crosslinked.

The carboxylic anionic, and preferably acrylic, polymer(s) may be present in the dye composition according to the invention in contents ranging from 0.01% to 10% by weight, in particular from 0.1% to 5% by weight and even better still from 0.5% to 2% by weight relative to the total weight of the composition.

According to another particular embodiment of the invention, the ingredient b) represents a mixture of thickening cellulose polymer(s) and carboxylic anionic polymer(s). Said mixture is preferably present in the dye composition according to the invention in contents ranging from 0.01% to 10% by weight, in particular from 0.1% to 5% by weight and even better still from 0.5% to 2% by weight relative to the total weight of the composition.

Additional Surfactants

The composition for dyeing keratin fibres according to the invention may also contain one or more additional or supplementary surfactants. According to one particular embodiment of the invention, the supplementary surfactant(s) are chosen from anionic, cationic or non-ionic, and amphoteric or zwitterionic surfactants, preferentially non-ionic or anionic surfactants, and even more preferentially non-ionic surfactants.

The composition of the invention may comprise one or more amphoteric surfactants.

The term "amphoteric or zwitterionic surfactant" means a surfactant comprising in its structure one or more cationic sites and one or more anionic sites.

The amphoteric or zwitterionic surfactant(s) that can be used in the present invention may especially be optionally quaternized secondary or tertiary aliphatic amine derivatives, in which the aliphatic group is a linear or branched chain comprising from 8 to 22 carbon atoms, said amine derivatives containing at least one anionic group such as, for example, a carboxylate, sulfonate, sulfate, phosphate or phosphonate group. Among the optionally quaternized secondary or tertiary aliphatic amine derivatives that may be used, as defined above, mention may be made of the compounds of respective structures (A3) and (A4) below:

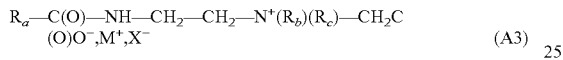
$$R_a\text{---}C(O)\text{---}NH\text{---}CH_2\text{---}CH_2\text{---}N^+(R_b)(R_c)\text{---}CH_2C(O)O^-,M^+,X^- \quad (A3)$$

in which formula (A3):
  $R_a$ represents a $C_{10}$-$C_{30}$ alkyl or alkenyl group derived from an acid $R_a$—COOH preferably present in hydrolysed coconut oil, or a heptyl, nonyl or undecyl group;
  $R_b$ represents a β-hydroxyethyl group; and
  $R_c$ represents a carboxymethyl group;
  $M^+$ represents a cationic counterion derived from an alkali metal or alkaline-earth metal, such as sodium, an ammonium ion or an ion derived from an organic amine, and
  $X^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$) alkylarylsulfonates, in particular methyl sulfate and ethyl sulfate; or alternatively $M^+$ and $X^-$ are absent;

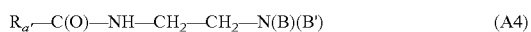
$$R_{a'}\text{---}C(O)\text{---}NH\text{---}CH_2\text{---}CH_2\text{---}N(B)(B') \quad (A4)$$

in which formula (A4):
  B represents the group —$CH_2$—$CH_2$—O—X';
  B' represents the group —$(CH_2)_z$Y', with z=1 or 2;
  X' represents the group —$CH_2$—C(O)OH, —$CH_2$—C(O) OZ', —$CH_2$—$CH_2$—C(O)OH, —$CH_2$—$CH_2$—C(O) OZ', or a hydrogen atom;
  Y' represents the group —C(O)OH, —C(O)OZ', —$CH_2$—CH(OH)—$SO_3$H or the group —$CH_2$—CH(OH)—$SO_3$—Z';
  Z' represents a cationic counterion derived from an alkali metal or alkaline-earth metal, such as sodium, an ammonium ion or an ion derived from an organic amine;
  $R_{a'}$ represents a $C_{10}$-$C_{30}$ alkyl or alkenyl group of an acid $R_{a'}$—C(O)OH preferably present in coconut oil or in hydrolysed linseed oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

By way of example, mention may be made of the cocoamphodiacetate sold by the company Rhodia under the trade name Miranol® C2M Concentrate.

More particularly, the amphoteric or zwitterionic surfactant(s) are chosen from the betaine surfactants of formula (A5), and also the acid or base salts thereof, and solvates thereof such as hydrates:

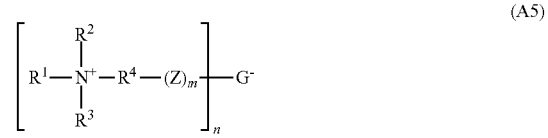

(A5)

in which formula (A5):
  $R^1$ denotes a saturated or unsaturated, linear or branched hydrocarbon-based chain comprising from 6 to 100 carbon atoms and in particular from 6 to 50 carbon atoms, which may be interrupted with one or more heteroatoms, divalent groups, or combinations thereof chosen from —O—, —C(O)— and —N(R)—; with R denoting a hydrogen atom or a $C_1$-$C_4$ alkyl radical, and $R^1$ also possibly being interrupted with an arylene group or terminated with an aryl group;
  $R^2$ and $R^3$, which may be identical or different, in particular $R^2$ and $R^3$ are identical, denote a ($C_1$-$C_6$)alkyl group; preferably, $R^2$ and $R^3$ represent a methyl group;
  $R^4$ denotes a linear or branched, preferably linear, divalent hydrocarbon-based radical comprising from 1 to 10 and preferably from 1 to 5 carbon atoms, optionally substituted in particular with one or more hydroxyl groups;
  Z denotes a heteroatom or a divalent group chosen from —O— and —N(R)— with R as defined previously,
  n denotes a number equal to 1 or 2;
  m denotes an integer equal to 0 or 1;
  $G^-$ denotes an anionic radical chosen from carboxylates, sulfates, sulfonates, phosphates and phosphonates (*—C(O)—O$^-$, *—S(O)$_2$—O$^-$, *—O—S(O)$_2$—O$^-$, *—P(O)$_2$—O$^-$, *—P(O)—O$_2^-$, *—P(OH)—O$^-$, =P(O)—O$^-$ and =P—O$^-$; with "*-" denoting the point of attachment of the anionic radical to the rest of the molecule via Z or $R^4$ when n is 1, and "**=" representing the two points of attachment of the anionic radical via Z or $R^4$ when n is 2);
  it being understood that:
    when n is 2, the radicals $R^1R^2R^3N^+$—R'—(Z)$_m$— are identical or different, preferably identical; and
    the surfactant of formula (A5) being electrically neutral, it may comprise anionic and/or cationic counterions to produce the electrical neutrality of the molecule.

The term "unsaturated" hydrocarbon-based chain means a hydrocarbon-based chain which comprises one or more double bonds and/or one or more triple bonds, said bonds possibly being conjugated or unconjugated.

The term "alkyl radical" means a saturated linear or branched hydrocarbon-based radical, preferably of $C_1$-$C_8$.

The term "alkenyl radical" means a linear or branched, preferably $C_2$-$C_8$, hydrocarbon-based radical; which is unsaturated, comprising one or more conjugated or unconjugated double bonds.

The term "alkoxy radical" means an alkyl-oxy radical for which the alkyl radical is a linear or branched $C_1$-$C_{16}$ and preferentially $C_1$-$C_8$ hydrocarbon-based radical.

The term "aryl" radical means a fused or non-fused monocyclic or polycyclic carbon-based group comprising from 6 to 22 carbon atoms, and in which at least one ring is aromatic; preferentially, the aryl radical is a phenyl, biphenyl, naphthyl, indenyl, anthracenyl or tetrahydronaphthyl.

The term "arylene" radical means a fused or non-fused monocyclic or polycyclic, divalent aromatic carbon-based radical comprising from 6 to 22 carbon atoms, and in which at least one ring is aromatic, preferably phenylene and more preferentially 1,3-phenylene or 1,4-phenylene.

The term "optionally substituted" attributed to the radical in question means that said radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom.

According to one preferred embodiment of the invention, the betaine surfactant(s) are chosen from the surfactants of formula (A5) in which n is equal to 1 and $G^-$ denotes an anionic radical chosen from *—C(O)O— and *—S(O)$_2$—O$^-$.

According to an advantageous embodiment of the invention, the betaine surfactant(s) are chosen from the surfactants of formula (I) in which $R^4$ denotes a linear $C_1$-$C_5$ divalent alkylene radical optionally substituted with a hydroxyl group, such as —CH$_2$—CH$_2$—CH$_2$—, —CH$_2$—CH(OH)—CH$_2$— or —CH$_2$—CH$_2$—.

According to one preferred embodiment of the invention, the betaine surfactant(s) are chosen from the surfactants of formula (A5) in which m is 1 and Z represents an oxygen atom or a group —N(R)— with R as defined previously. More preferentially, when m is 1, then Z represents an oxygen atom.

According to another preferred embodiment of the invention, the betaine surfactant(s) are chosen from the surfactants of formula (A5) in which m is 0.

According to another preferred embodiment of the invention, the betaine surfactant(s) are chosen from the surfactants of formula (A5) in which $R^1$ denotes a group chosen from i) $C_6$-$C_{30}$ alkyl; ii) $C_6$-$C_{30}$ alkenyl; -alkyl($C_6$-$C_{30}$)-amido-($C_1$-$C_4$)alkyl or -alkenyl($C_6$-$C_{30}$)-amido-($C_1$-$C_4$)alkyl, with amido representing a group —C(O)—N(R)— and R being as defined previously. Particularly, R denotes a hydrogen atom.

More particularly, $R^1$ denotes a linear or branched, preferably linear, $C_6$-$C_{30}$ alkyl radical.

More particularly, the betaine surfactant(s) that may be used in the present invention are chosen from ($C_8$-$C_{20}$)alkylbetaines, sulfobetaines, ($C_8$-$C_{20}$)alkylamido($C_3$-$C_8$)alkylbetaines and ($C_8$-$C_{20}$)alkylamido($C_6$-$C_8$)alkylsulfobetaines, better still from ($C_8$-$C_{20}$)alkylbetaines and ($C_8$-$C_{20}$)alkylamido($C_3$-$C_8$)alkylbetaines and even better still from ($C_8$-$C_{20}$)alkylbetaines.

Even more preferentially, the amphoteric or zwitterionic surfactant according to the invention is cocobetaine.

In the composition of the invention, the amount of amphoteric and zwitterionic surfactant(s) in the composition preferably ranges from 0.1% to 50% by weight and better still from 0.5% to 20% by weight relative to the total weight of the composition.

The term "anionic surfactant" means a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH and =PO$^-$, the anionic parts comprising a cationic counterion such as an alkali metal, an alkaline-earth metal or an ammonium.

Mention may be made, as examples of anionic surfactants which can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids, and the corresponding non-salified forms of all these compounds, the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Use is preferably made, among the anionic surfactants mentioned, of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

The cationic surfactant(s) which can be used in the composition according to the invention comprise, for example, salts of optionally polyoxyalkylenated primary, secondary or tertiary fatty amines, quaternary ammonium salts, and mixtures thereof.

Examples of quaternary ammonium salts that may especially be mentioned include:

those corresponding to general formula (A6) below:

(A6)

in which formula (A6):

$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and $X^-$ represents an organic or inorganic anionic counterion, such as that chosen from halides, acetates, phosphates, nitrates, ($C_1$-$C_4$)alkyl sulfates, ($C_1$-$C_4$)alkyl or ($C_1$-$C_4$) alkylaryl sulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, $C_1$-$C_{30}$ hydroxyalkyl groups, $X^-$ is an anionic counterion chosen from the group of halides, phosphates, acetates, lactates, ($C_1$-$C_4$)alkyl sulfates, and ($C_1$-$C_4$) alkyl- or ($C_1$-$C_4$)alkylarylsulfonates.

Among the quaternary ammonium salts of formula (A6), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly to, distearoylethylhydroxyethylmethylammonium methosulfate, dipalmitoylethylhydroxyethylammonium methosulfate or distearoylethylhydroxyethylammonium methosulfate, or else, lastly to, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, such as, for example, those of formula (A7) below:

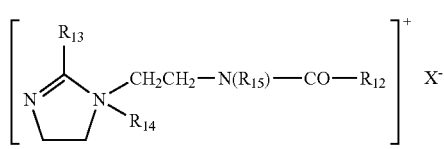

(A7)

in which formula (A7):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or inorganic anionic counterion, such as that chosen from halides, phosphates, acetates, lactates, ($C_1$-$C_4$)alkyl sulfates, ($C_1$-$C_4$)alkyl or ($C_1$-$C_4$) alkylaryl sulfonates.

$R_{12}$ and $R_{13}$ preferably denote a mixture of alkyl or alkenyl groups containing from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary diammonium or triammonium salts, particularly of formula (A8) below:

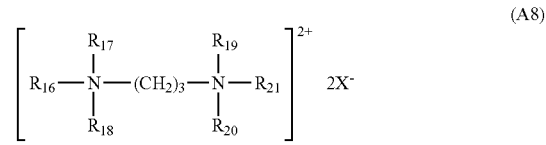

(A8)

in which formula (A8):

$R_{16}$ denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group —$(CH_2)_3$—$N^+$ ($R_{16a}$)($R_{17a}$)($R_{18a}$), $X^-$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$, which may be identical or different, represent an organic or inorganic anionic counterion, such as that chosen from halides, acetates, phosphates, nitrates, ($C_1$-$C_4$)alkyl sulfates, ($C_1$-$C_4$)alkyl or ($C_1$-$C_4$)alkylaryl sulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (A9) below:

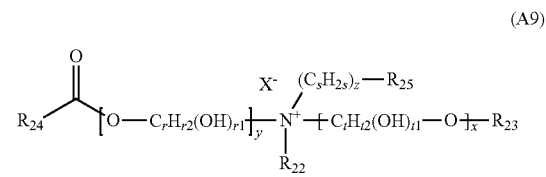

(A9)

in which formula (A9):

$R_{22}$ is chosen from $C_1$-$C_6$ alkyl groups and $C_1$-$C_6$ hydroxyalkyl or dihydroxyalkyl groups, $R_{23}$ is chosen from:

the group

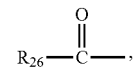

linear or branched, saturated or unsaturated $C_1$-$C_{22}$ hydrocarbon-based groups $R_{27}$, a hydrogen atom, $R_{25}$ is chosen from:

the group

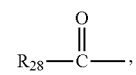

linear or branched, saturated or unsaturated $C_1$-$C_6$ hydrocarbon-based groups $R_{29}$, a hydrogen atom, $R_{24}$, $R_{26}$ and $R_{28}$, which may be identical or different, are selected from linear or branched, saturated or unsaturated $C_7$-$C_{21}$ hydrocarbon-based groups;

r, s and t, which may be identical or different, are integers ranging from 2 to 6, r1 and t1, which may be identical or different, are equal to 0 or 1, with r2+r1=2r and t1+t2=2t, y is an integer ranging from 1 to 10, x and z, which may be identical or different, are integers ranging from 0 to 10, X⁻ represents an organic or inorganic anionic counterion, with the proviso that the sum x+y+z equals from 1 to 15, that, when x is 0, then $R_{23}$ denotes $R_{27}$ and that, when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z has a value from 1 to 10.

When $R_{23}$ is an $R_{27}$ hydrocarbon-based group, it may be long and may contain from 12 to 22 carbon atoms, or may be short and may have from 1 to 3 carbon atoms.

When $R_{25}$ is an $R_{29}$ hydrocarbon-based group, it preferably contains 1 to 3 carbon atoms.

Advantageously, $R_{24}$, $R_{26}$ and $R_{28}$, which are identical or different, are selected from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion X⁻ is preferably a halide, such as chloride, bromide or iodide; a ($C_1$-$C_4$)alkyl sulfate or a ($C_1$-$C_4$)alkyl- or ($C_1$-$C_4$)alkylarylsulfonate. However, it is possible to use methanesulfonate, phosphate, nitrate, tosylate, an anion derived from an organic acid, such as acetate or lactate, or any other anion compatible with the ammonium comprising an ester function.

The anionic counterion X⁻ is even more particularly chloride, methyl sulfate or ethyl sulfate.

Use is made more particularly, in the composition according to the invention, of the ammonium salts of formula (A9) in which:

$R_{22}$ denotes a methyl or ethyl group, x and y are equal to 1, z is equal to 0 or 1, r, s and t are equal to 2, $R_{23}$ is chosen from:

the group

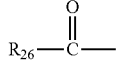

methyl, ethyl or $C_{14}$-$C_{22}$ hydrocarbon-based groups, a hydrogen atom, $R_{25}$ is chosen from:

the group

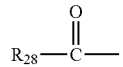

a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based radicals are linear.

Among the compounds of formula (A9), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably have from 14 to 18 carbon atoms and originate more particularly from a vegetable oil, such as palm oil or sunflower oil. When the compound comprises several acyl groups, the latter can be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of vegetable or animal origin, or by transesterification of the methyl esters thereof. This esterification is followed by a quaternization by means of an alkylating agent, such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of monoesters, diesters and triesters with a weight majority of diester salts.

It is also possible to use the ammonium salts containing at least one ester function that are described in U.S. Pat. No. 4,874,554 and U.S. Pat. No. 4,137,180.

Use may be made of behenoylhydroxypropyltrimethylammonium chloride, sold by Kao under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride and dipalmitoylethylhydroxyethylammonium methosulfate, and mixtures thereof.

Examples of non-ionic surfactants that can be used in the composition used according to the invention are described, for example, in the "Handbook of Surfactants" by M. R. Porter, published by Blackie & Son (Glasgow and London), 1991, pp. 116-178. They are especially chosen from alcohols, α-diols and ($C_1$-$C_{20}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkylglucamine and of N-acylmethylglucamine, aldobionamides and amine oxides.

According to one advantageous variant of the invention, the dye composition comprises one or more non-ionic surfactants preferably chosen from mono- or polyoxyalkylenated, mono- or polyglycerolated non-ionic surfactants. The oxyalkylene units are more particularly oxyethylene or oxypropylene units, or a combination thereof, preferably oxyethylene units.

Mention may be made, as examples of oxyalkylenated non-ionic surfactants, of:
oxyalkylenated ($C_8$-$C_{24}$)alkylphenols;
saturated or unsaturated, linear or branched, oxyalkylenated $C_8$-$C_{30}$ alcohols;
saturated or unsaturated, linear or branched, oxyalkylenated $C_8$-$C_{30}$ amides;
esters of saturated or unsaturated, linear or branched, $C_8$-$C_{30}$ acids and of polyethylene glycols;
polyoxyethylenated esters of saturated or unsaturated, linear or branched, $C_8$-$C_{30}$ acids and of sorbitol;
saturated or unsaturated oxyethylenated vegetable oils;
condensates of ethylene oxide and/or of propylene oxide, inter alia, alone or as mixtures;
oxyethylenated and/or oxypropylenated silicones.

The surfactants contain a number of moles of ethylene oxide and/or of propylene oxide of between 1 and 100, preferably between 2 and 50 and preferably between 2 and 30. Advantageously, the non-ionic surfactants do not comprise any oxypropylene units.

In accordance with one preferred embodiment of the invention, the oxyalkylenated non-ionic surfactants are chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide.

As examples of monoglycerolated or polyglycerolated non-ionic surfactants, monoglycerolated or polyglycerolated $C_8$-$C_{40}$ alcohols are preferably used.

In particular, the monoglycerolated or polyglycerolated $C_8$-$C_{40}$ alcohols correspond to formula (A10) below:

$$R_{29}O\text{---}[CH_2\text{---}CH(CH_2OH)\text{---}O]_m\text{---}H \quad (A10)$$

in which formula (A10):
$R_{29}$ represents a linear or branched $C_8$-$C_{40}$ and preferably $C_8$-$C_{30}$ alkyl or alkenyl radical; and
m represents a number ranging from 1 to 30 and preferably from 1 to 10.

As examples of compounds of formula (A10) that are suitable within the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A10) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

Preferably, the surfactant(s) are chosen from non-ionic surfactants or from anionic surfactants.

According to one variant of the invention, the composition and the process for treating (dyeing) keratin fibres use one or more surfactants chosen from mono- or polyoxyalkylenated non-ionic surfactants, and/or one or more anionic surfactants, in particular of alkyl sulfate type.

According to another variant of the invention, the additional surfactant(s) present in the composition are chosen from non-ionic surfactants different from the (poly)alkoxylated or (poly)glycerolated fatty alcohols b) as previously defined.

In the composition of the invention, the amount of additional surfactant(s) in the composition preferably ranges from 0.1% to 50% by weight and better still from 0.5% to 20% by weight relative to the total weight of the composition.

Preferably, the surfactant(s) are chosen from non-ionic surfactants or from anionic surfactants. More particularly, the surfactant(s) present in the composition are chosen from non-ionic surfactants.

According to one variant of the invention, the composition and the process for treating (dyeing) keratin fibres use one or more surfactants chosen from non-ionic surfactants, in particular mono- or polyoxyalkylenated non-ionic surfactants, and/or one or more anionic surfactants, in particular of alkyl sulfate type.

Even more preferentially, the non-ionic surfactants are chosen from polyoxyethylenated fatty alcohols.

In the composition of the invention, the amount of additional surfactant(s) in the composition preferably ranges from 0.1% to 50% by weight and even better still from 0.5% to 20% by weight relative to the total weight of the composition.

c) (2,5-Diaminophenyl)ethanol Oxidation Bases:

The composition of the invention comprises c) one or more oxidation bases chosen from (2,5-diaminophenyl)ethanol (or 2-β-hydroxyethyl-para-phenylenediamine) of the following formula, and also acid salts thereof or solvates thereof such as hydrates:

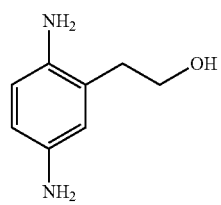 [SMILES: Nc1ccc(N)c(CCO)c1]

The oxidation base(s) chosen from (2,5-diaminophenyl) ethanol and also acid salts thereof or solvates thereof such as hydrates, according to the invention, are advantageously in an amount ranging from 0.0001% to 20% by weight relative to the total weight of the composition, preferably from 0.005% to 10% by weight and more particularly from 0.01% to 10% by weight relative to the total weight of the composition.

The composition according to the invention may comprise one or more additional oxidation bases, i.e. oxidation bases other than (2,5-diaminophenyl)ethanol, acid salts thereof or solvates thereof such as hydrates. According to one particular embodiment of the invention, the additional base(s) are chosen from heterocyclic bases and benzene bases, and the addition salts thereof.

The benzene oxidation bases according to the invention are particularly chosen from para-phenylenediamines, bis(phenyl)alkylenediamines, para-aminophenols and ortho-aminophenols, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine or PPD, para-tolylenediamine or PTD, 2-isopropyl-para-phenylenediamine, 2-β-hydroxyethyl-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Mention may be made, among ortho-aminophenols, by way of example, of 2-aminophenol, 2-amino-5-methylphenol, 2-amino-6-methylphenol, 5-acetamido-2-aminophenol and the addition salts thereof.

The heterocyclic bases according to the invention are more particularly chosen from pyridine derivatives, pyrimidine derivatives and pyrazole derivatives, and the addition salts thereof.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the dyeing process according to the invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Mention may be made, among pyrazole derivatives, of the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and their addition salts. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof.

Mention may also be made, as pyrazole derivatives, of diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

The additional oxidation base(s) according to the invention each advantageously represent from 0.0001% to 10% by weight relative to the total weight of the composition, and preferably from 0.005% to 5% by weight relative to the total weight of the composition.

d) Additional Couplers

The composition of the invention may optionally comprise one or more couplers. According to one preferred embodiment, the composition and the process use one or more couplers. Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(6-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The coupler(s) each advantageously represent from 0.0001% to 10% by weight, relative to the total weight of the composition, and preferably from 0.005% to 5% by weight, relative to the total weight of the composition of the invention.

In general, the addition salts of the oxidation bases and couplers which can be used in the context of the invention are selected in particular from the addition salts with an acid, such as the hydrochlorides, hydrobromides, sulfates, citrates, succinates, tartrates, lactates, tosylates, benzenesulfonates, phosphates and acetates.

In one variant of the invention, the composition does not contain any para-phenylenediamine (PPD) and/or the process for treating keratin fibres does not use PPD. According to another advantageous embodiment, the composition and/or the process for treating keratin fibres do not use chlorinated bases or halogenated couplers, in particular chlorinated bases or couplers such as those chosen from 2-amino-6-chloro-4-nitrophenol, 2,6-dichloro-4-aminophenol, 2-chloro-6-ethylamino-4-nitrophenol, 3-amino-5-chloroaniline, 2-chloro-4-aminophenol and 2-chloro-6-methyl-3-aminophenol. According to another particular embodiment, the composition and/or the process for treating keratin fibres do not use 3-(2,4-diaminophenoxy)-1-propanol couplers.

Additional Dyes

The composition of the invention may also comprise one or more direct dyes. The latter are more particularly chosen from ionic or non-ionic entities, preferably cationic or non-ionic entities. These direct dyes may be synthetic or of natural origin.

Examples of suitable direct dyes that may be mentioned include azo direct dyes; methine direct dyes; carbonyl direct dyes; azine direct dyes; nitro(hetero)aryl direct dyes; tri(hetero)arylmethane direct dyes; porphyrin direct dyes; phthalocyanin direct dyes, and natural direct dyes, alone or as mixtures.

More particularly, the azo dyes comprise an —N═N— function in which the two nitrogen atoms are not simultaneously engaged in a ring. However, it is not excluded for one of the two nitrogen atoms of the sequence —N═N— to be engaged in a ring.

The dyes of the methine family are more particularly compounds comprising at least one sequence chosen from >C═C< and —N═C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, monoarylmethanes and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanine type, use may be made of cationic or non-cationic compounds optionally comprising one or more metals or metal ions, such as, for example, alkali and alkaline earth metals, zinc and silicon.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanin direct dyes, porphyrin direct dyes and natural direct dyes, alone or as mixtures.

Among the natural dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin, haematin, haematoxylin, brasilin, brasilein and orceins. Use may also be made of extracts or decoctions comprising these natural dyes and in particular henna-based poultices or extracts.

When they are present, the direct dye(s) more particularly represent from 0.0001% to 10% by weight and preferably from 0.005% to 5% by weight of the total weight of the composition.

e) Additional Basifying Agents:

The composition of the invention may also comprise e) one or more basifying agents. According to one embodiment of the invention, the composition and the process for treating keratin fibres use one or more basifying agents. The basifying agent(s) may be inorganic or organic or hybrid.

The inorganic basifying agent(s) are preferably chosen from aqueous ammonia, alkali metal carbonates or bicarbonates such as sodium carbonate or bicarbonate, potassium carbonate or bicarbonate, sodium hydroxide or potassium hydroxide, or their mixtures.

The organic basifying agent(s) is (are) preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise an alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds of formula (A11) below:

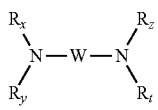

(A11)

in which formula (A11) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (A11) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

The organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids can be in the neutral or ionic form.

Mention may in particular be made, as amino acids which can be used in the present invention, of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (A12) below:

(A12)

in which formula (A12) R represents a group chosen from: imidazolyl, preferably 4-imidazolyl; —$(CH_2)_3NH_2$; —$(CH_2)_2NH_2$; —$(CH_2)_2$—NH—C(O)—$NH_2$; and

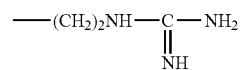

The compounds corresponding to formula (A12) are histidine, lysine, arginine, ornithine and citrulline.

The organic amine can also be chosen from organic amines of heterocyclic type. Mention may in particular be made, in addition to histidine, already mentioned in the amino acids, of pyridine, piperidine, imidazole, triazole, tetrazole or benzimidazole.

The organic amine can also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that can be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Use may in particular be made of guanidine carbonate or monoethanolamine hydrochloride.

Preferably, the alkaline agent(s) present in the composition of the invention are chosen from alkanolamines, amino acids in neutral or ionic form, in particular basic amino acids, and preferably corresponding to those having the formula (III). Even more preferentially, the basifying agent(s) are chosen from monoethanolamine (MEA) and basic amino acids in neutral or ionic form.

Advantageously, the composition according to the invention has a content of basifying agent(s) ranging from 0.01% to 30% by weight and preferably from 0.1% to 20% by weight relative to the weight of the composition.

According to a first particular embodiment, the composition does not contain aqueous ammonia or a salt thereof or the process according to the invention does not use any aqueous ammonia, or a salt thereof, as basifying agent.

If, however, according to another particular embodiment, the composition or the process did use any, its content would advantageously not exceed 0.03% by weight (expressed as $NH_3$) and would preferably not exceed 0.01% by weight relative to the weight of the composition of the invention. Preferably, if the composition comprises aqueous ammonia, or a salt thereof, then the amount of basifying agent(s) other than the aqueous ammonia is greater than that of the aqueous ammonia (expressed as $NH_3$).

f) Chemical Oxidizing Agent

The composition of the invention comprises f) one or more chemical oxidizing agents. The term "chemical oxidizing agent" means an oxidizing agent other than atmospheric oxygen. The composition of the invention preferably contains one or more chemical oxidizing agents.

More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline earth metal percarbonates.

This oxidizing agent is advantageously constituted of hydrogen peroxide.

The concentration of chemical oxidizing agents may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Solvent

The composition according to the invention can also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight, with respect to the weight of the composition.

Other Additives

The composition according to the invention may also contain various adjuvants conventionally used in hair dyeing compositions, such as anionic, cationic, non-ionic, amphoteric or zwitterionic polymers or mixtures thereof other than the polymers b); inorganic thickeners, and in particular fillers such as clays or talc; organic thickeners with, in particular, anionic polymeric associative thickeners other than the polymers of b), cationic, non-ionic and amphoteric polymeric associative thickeners other than the polymers b); antioxidants; penetrants; sequestrants; fragrances; dispersants; film-forming agents; ceramides; preservatives; opacifiers.

The above adjuvants are generally present in an amount, for each of them, of between 0.01% and 20% by weight relative to the weight of the composition.

The composition may especially comprise one or more inorganic thickeners chosen from organophilic clays and fumed silicas, or their mixtures.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas can be obtained by high-temperature hydrolysis of a volatile silicon compound in an oxyhydrogen flame, producing a finely divided silica. This process makes it possible in particular to obtain hydrophilic silicas which exhibit a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica by chemical reaction for the purpose of reducing the number of silanol groups. It is possible in particular to replace silanol groups with hydrophobic groups; a hydrophobic silica is then obtained.

The hydrophobic groups can be:
trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by the company Degussa and Cab-O-Sil TS-530® by the company Cabot;
dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by Degussa and Cab-O-Sil TS-610® and Cab-O-Sil TS-720® by Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the inorganic thickener represents from 1% to 30% by weight relative to the weight of the composition.

The composition may also comprise one or more organic thickeners other than the polymers b).

These thickeners may be chosen from fatty acid amides (coconut acid diethanolamide or monoethanolamide, oxyethylenated alkyl ether carboxylic acid monoethanolamide), polymeric thickeners, such as guar gum and derivatives thereof (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic regions and hydrophobic regions having a fatty chain (alkyl or alkenyl chain comprising at least 10 carbon atoms) which are capable, in an aqueous medium, of reversibly associating with each other or with other molecules).

According to one particular embodiment, the additional organic thickener is chosen from guar gum and derivatives thereof (hydroxypropyl guar), gums of microbial origin (xanthan gum, scleroglucan gum) and crosslinked homopolymers of acrylic acid or of acrylamidopropanesulfonic acid.

The content of additional organic thickener(s) other than the polymers b), if they are present, usually ranges from 0.01% to 20% by weight and preferably from 0.1% to 5% by weight relative to the weight of the composition.

The composition of the invention may be in various forms, for instance a solution, an emulsion (milk or cream) or a gel, preferably in the form of an emulsion and particularly of a direct emulsion.

According to one preferred embodiment, the composition according to the invention comprises one or more non-silicone liquid fatty substances, one or more acrylic anionic polymers and/or one or more thickening cellulose polymers, one or more oxidation bases chosen from (2,5-diaminophenyl)ethanol and also acid salts thereof or solvates thereof such as hydrates, one or more couplers, one or more basifying agent(s) and one or more chemical oxidizing agent(s), said composition comprising in total at least 10% by weight of fatty substances relative to the total weight of the composition.

Preferably, the composition according to the invention comprises one or more non-silicone liquid fatty substances, one or more non-associative acrylic anionic polymers and/or one or more thickening cellulose polymers, one or more oxidation bases chosen from (2,5-diaminophenyl)ethanol and also acid salts thereof or solvates thereof such as hydrates, one or more couplers, one or more basifying agent(s), and one or more chemical oxidizing agent(s).

Even more preferentially, the composition according to the invention comprises:
one or more non-silicone liquid fatty substance(s) chosen from $C_6$-$C_{16}$ hydrocarbons, hydrocarbons containing more than 16 carbon atoms, triglycerides, fatty alcohols, liquid esters of fatty acids and/or of fatty alcohols, or mixtures thereof,
one or more non-associative acrylic anionic polymer(s) chosen from acrylic acid homopolymers which are preferably crosslinked,
one or more oxidation base(s) chosen from (2,5-diaminophenyl)ethanol and also acid salts thereof or solvates thereof such as hydrates,
one or more coupler(s),
one or more basifying agent(s) and
one or more chemical oxidizing agent(s).

Processes of the Invention

The composition according to the invention comprising the ingredients a) to f) as defined previously is applied to dry or wet keratin fibres. It is left in place on the fibres for a time generally of from 1 minute to 1 hour and preferably from 5 minutes to 30 minutes.

The temperature during the dyeing process is conventionally between ambient temperature (between 15° C. and 25° C.) and 80° C. and preferably between ambient temperature and 60° C.

After the treatment, the human keratin fibres are optionally rinsed with water, optionally washed with a shampoo and then rinsed with water, before being dried or left to dry.

The composition according to the invention is generally prepared by mixing at least two compositions.

In a first variant of the invention, the composition according to the invention comprising the ingredients a) to f) as defined previously results from the mixing of two compositions:
a composition (A) comprising c) at least one oxidation base chosen from (2,5-diaminophenyl)ethanol and also acid salts thereof or solvates thereof such as hydrates; d) optionally at least one coupler as defined previously; e) at least one basifying agent as defined previously; and
a composition (B) comprising f) at least one chemical oxidizing agent as defined previously,
it being understood that:
at least one of the compositions (A) or (B) comprises a) at least one fatty substance which is preferably liquid and non-silicone as defined previously, and b) at least one cellulose polymer as defined previously and/or one or more carboxylic anionic, and preferably acrylic, polymers as defined previously, such that the composition according to the invention resulting from the mixing of compositions (A)+(B) comprises at least 10% by weight, preferably at least 15% by weight, better still at least 20% by weight and even better still at least 25% by weight of fatty substances relative to the total weight of the mixture of (A)+(B).

Preferentially, at least one of the compositions (A) or (B) is aqueous.

Even more preferentially, both the compositions (A) and (B) are aqueous.

The term "aqueous composition" means a composition comprising at least 5% water. Preferably, an aqueous composition comprises more than 10% by weight of water and even more advantageously more than 20% by weight of water.

Preferably, composition (A) is aqueous.

In this variant, composition (A) comprises at least 50% of fatty substances and even more preferentially at least 50% of non-silicone fatty substances that are liquid at ambient temperature (25° C.).

Preferably, composition (A) is a direct or inverse emulsion and preferably a direct (O/W) emulsion.

In this variant, compositions (A) and (B) are preferably mixed in an (A)/(B) weight ratio ranging from 0.2 to 10 and better still from 0.5 to 2.

In a second variant of the invention, the composition according to the invention comprising ingredients a) to f) as defined previously results from the mixing of three compositions, the three compositions being aqueous or at least one of them being anhydrous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of said composition. It should be noted that the water present in the composition is more particularly "bound water", such as the water of crystallization of the salts or traces of water absorbed by the raw materials used in the preparation of the compositions according to the invention.

In this second variant, use will preferably be made of two aqueous compositions (B') and (C') and an anhydrous composition (A'). The anhydrous composition (A') then preferably comprises a) at least one fatty substance as defined previously and more preferentially at least one liquid fatty substance. Composition (B') then preferably comprises c) at least the oxidation base chosen from (2,5-diaminophenyl) ethanol and also acid salts thereof or solvates thereof such as hydrates and d) optionally at least one coupler as defined previously. Composition (C') then preferably comprises f) at least one chemical oxidizing agent as defined previously. The basifying agent(s) e) as defined previously are included in the compositions (A') and/or (B') and preferably solely in composition (B'). The cellulose polymer(s) as defined previously and/or the carboxylic anionic and preferably acrylic polymer(s) as defined previously are included in at least one of the compositions (A'), (B') or (C'), these three compositions being such that the fatty substance content of the composition according to the invention resulting from the mixing of the three compositions (A')+(B')+(C') comprises at least 10% by weight, preferably at least 15% by weight, better still at least 20% by weight and even better still at least 25% by weight relative to the total weight of the mixture of the three compositions (A')+(B')+(C').

In this variant, the compositions (A'), (B') and (C') are preferably mixed in an (A')+(B')/(C') weight ratio ranging from 0.2 to 10 and better still from 0.5 to 2 and in an (A')/(B') weight ratio ranging from 0.5 to 10 and better still from 1 to 5.

In accordance with this second variant, the dyeing process therefore consists in applying to the keratin fibres the dye composition resulting from the mixing of the compositions (A'), (B') and (C') mentioned above.

Dyeing Device

Finally, the invention relates to a first multi-compartment device comprising a first compartment containing composition (A) as described above and at least a second compartment containing composition (B) as described above, the compositions of the compartments being intended to be mixed before application to give the formulation after mixing according to the invention, provided that the amount of fatty substance in this formulation represents at least 10% by weight, in particular at least 15% by weight, more particularly at least 20% by weight and preferentially at least 25% by weight relative to the weight of the formulation resulting from the mixing of (A)+(B).

The invention also relates to a second multi-compartment device comprising a first compartment containing composition (A') as described above and a second compartment containing a cosmetic composition (B') as described above and at least a third compartment comprising composition (C') as described above, the compositions of the compartments being intended to be mixed before application to give the formulation after mixing according to the invention, provided that the amount of fatty substance in this formulation represents at least 10% by weight, in particular at least 15% by weight, more particularly at least 20% by weight and preferentially at least 25% by weight relative to the weight of the formulation resulting from the mixing of (A')+(B')+(C').

The evaluation of the coloration can be done visually or read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis. The lower the value of L, the darker or more intense the color. The higher the value of a*, the redder the shade; the higher the value of b*, the yellower the shade. The variation in coloring between the colored locks of natural white hair (NW) which is untreated (control) and after treatment or coloration are defined by $\Delta E^*$, corresponding to the colour uptake on keratin fibers, according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural hair comprising 90% of white hairs and $L_o^*$, $a_o^*$ and $b_o^*$ represent the values measured for the untreated natural hair comprising 90% of white hairs.

The greater the value of $\Delta E$, the greater the difference in color between the control locks and the dyed locks and the greater colour uptake is.

On the other hand for evaluating the selectivity of the color between the root and tip of the keratin fiber, measurement can be done on permed or sensibilised white hair (PW) and natural white hair, wherein the variation in coloring between the colored locks PW and the colored natural white hair are defined by $\Delta E^*$, corresponding to the selectivity of the colour, is calculated according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural hair comprising 90% of white hairs and $L_o^*$, $a_o^*$ and $b_o^*$ represent the values measured after dyeing the permed or sensibilised hair. The lowest $\Delta E^*$, the best homogeneity of the hair color.

If the light fastness is investigated, $\Delta E^*$ is also calculated for the $L_o^*$, $a_o^*$, $b_o^*$ and L*, a*, b* measured of the locks before and after exposure to the light, respectively.

Chromaticity in the CIE L*, a*, b* colorimetric system is calculated according to the following equation:

$$C^* = \sqrt{a^{*2} + b^{*2}}$$

The greater the value of C*, the greater the chromaticity is.

The examples that follow serve to illustrate the invention without, however, being limiting in nature.

EXAMPLES

Example 1

| Ingredients | A1 | A2 |
|---|---|---|
| Liquid petroleum jelly (fatty substance a) | 60 | 59.7 |
| Safflower oil (triglycerides of palmitic-oleic-linoleic acids 6/12/78) (fatty substance a) | — | 0.1 |
| Tamanu kernel oil (fatty substance a) | — | 0.1 |
| Argan oil (fatty substance a) | — | 0.1 |
| Hydroxyethylcellulose (MW: 1.300.000) (polymer b) | 2.5 | — |
| Cationic hydroxyethylcellulose (Softcat SL 100 from Amerchol) (polymer b) | | 0.2 |
| 6-hydroxybenzomorpholine | 0.033 | 0.033 |
| 1--Hydroxyethyloxy-2,4-diaminobenzene dihydrochloride (coupler d) | 0.02 | 0.02 |
| 1,3-Dihydroxybenzene (resorcinol) (coupler d) | 0.67 | 0.67 |
| 1-Hydroxy-3-aminobenzene (coupler d) | 0.12 | 0.12 |
| 2-(2,5-Diaminophenyl)ethanol sulfate (oxidation base c) | 1.58 | 1.58 |

| Ingredients | A3 |
|---|---|
| Liquid petroleum jelly (fatty substance a) | 60 |
| Oxyethylenated (40 OE) hydrogenated castor oil | 1 |
| 6-hydroxybenzomorpholine | 0.033 |
| 1-β-Hydroxyethyloxy-2,4-diaminobenzene dihydrochloride | 0.02 |
| 1,3-Dihydroxybenzene (resorcinol) | 0.67 |
| 1-Hydroxy-3-aminobenzene | 0.12 |
| 2-(2,5-Diaminophenyl)ethanol sulfate (oxidation base c) | 1.58 |
| Diethylenetriaminepentaacetic acid, pentasodium salt as an aqueous 40% solution | 2 |
| Hydroxyethylcellulose (MW: 1.300.000) | 2.5 |
| Powdered sodium metabisulfite | 0.5 |
| Cocoylbetaine at 30% as an aqueous solution | 10 |
| Oxyethylenated (2 OE) stearyl alcohol | 0.1 |
| Oxyethylenated (20 OE) stearyl alcohol | 0.1 |
| Sodium lauryl ether sulfate (2.2 OE) at 70% as an aqueous solution | 2.5 |
| Antioxidant | 0.5 |
| Deionized water | q.s. for 100 |

Oxidizing Compositions B1, B2 and B3:

| Ingredients | B1 | B2 |
|---|---|---|
| Liquid petroleum jelly (fatty substance a) | — | 20 |
| Hydrogen peroxide as an aqueous 50% solution (200 vol. aqueous hydrogen peroxide solution) (oxidizing agent f) | 15 | 12 |
| Poly[(dimethyliminio)-1,3-propanediyl(dimethyliminio)-1,6-hexanediyl dichloride] as an aqueous 60% solution | | 0.25 |
| Polydimethyldiallylammonium chloride at 40% in water | | 0.5 |
| Dimethyldiallylammonium chloride/acrylic acid copolymer (80/20) at 40.5 as an aqueous solution | 0.74 | |
| Glycerol | 4 | 0.5 |
| Cetylstearyl alcohol (30/70 $C_{16}/C_{18}$) | | 6 |
| Oxyethylenated (20 OE) stearyl alcohol | | 5 |
| (50/50 $C_8/C_{10}$) alkyl polyglucoside (2) as an aqueous 60% solution | 3 | |
| Tetrasodium pyrophosphate decahydrate | 0.04 | 0.03 |
| Sodium salicylate | 0.035 | |
| Protected oxyethylenated (4 OE) rapeseed acid amide | | 1.3 |
| Vitamin E DL-Alpha-Tocopherol | | 0.1 |
| Disodium tin hexahydroxide | | 0.04 |
| Sequestrant | 0.06 | 0.15 |
| Deionized water | q.s. for 100 | q.s. for 100 |

-continued

| Ingredients | A1 | A2 |
|---|---|---|
| Pure monoethanolamine (basifying agent e) | 5.16 | 4.39 |
| Cocoylbetaine at 30% as an aqueous solution | 10 | — |
| Oxyethylenated (2 OE) stearyl alcohol | 0.1 | 1.13 |
| Oxyethylenated (20 OE) stearyl alcohol | 0.1 | 3.88 |
| Oxyethylenated (40 OE) hydrogenated castor oil | 1 | — |
| Sodium lauryl ether sulfate (2.2 OE) at 70% as an aqueous solution | 2.5 | |
| (50/50 $C_8/C_{10}$) Alkyl polyglucoside as an aqueous 60% solution | — | 4 |
| Oxyethylenated (4 OE) sorbitan monolaurate | — | 2.4 |
| Sequestrant | 2.2 | |
| Reducing agent | 0.5 | 0.45 |
| Fragrance | — | 0.72 |
| Deionized water | q.s. for 100 | q.s. for 100 |

| Ingredients | B3 |
|---|---|
| Hydrogen peroxide as a 50% solution (200 vol. aqueous hydrogen peroxide solution) (oxidizing agent f) | 6 |
| Etidronic acid, tetrasodium salt, as an aqueous 30% solution | 0.2 |
| Tetrasodium pyrophosphate decahydrate | 0.04 |
| Sodium salicylate | 0.035 |
| Dimethyldiallylammonium chloride/acrylic acid copolymer (80/20) at 40.5 as an aqueous solution | 0.74 |
| (50/50 $C_8/C_{10}$)Alkyl polyglucoside (2) as an aqueous 60% solution | 3 |
| Glycerol | 4 |
| Deionized water | q.s. for 100 |

The following compositions are prepared in which the amounts are expressed in grams of materials in their given state.

The dyeing compositions A1, A2 or A3 are mixed, respectively, with the oxidizing formulations B1, B2 or B3 respectively according to the ratio of 1 part of dyeing composition for 1 part of oxidizing composition.

The mixtures A1+B1, A2+B1 and A3+B3 obtained are then applied to hair comprising 90% white hairs. The "mixture/lock" bath ratio is 10/1 (g/g). The leave-on time is 35 minutes at 27° C.

After the leave-on time, the hair is rinsed with clear water and a shampoo is applied.

After drying, a light chestnut-brown shade of good strength and coverage is obtained on the hair.

Example 2

The following compositions are prepared in which the amounts are expressed in grams of materials in their given state.

2.1 Dyeing Compositions
a. Dyeing Composition A4:

| Composition | A4 |
| --- | --- |
| Liquid petroleum jelly (fatty substance a) | 60 |
| Cetyl palmitate (fatty substance a) | 2 |
| 2-(2,5-Diaminophenyl)ethanol sulfate (oxidation base c) | 1.58 |
| 6-Hydroxybenzomorpholine (coupler d) | 0.033 |
| 1-β-Hydroxyethyloxy-2,4-diaminobenzene dihydrochloride (coupler d) | 0.02 |
| 1,3-Dihydroxybenzene (resorcinol) (coupler d) | 0.67 |
| 1-Hydroxy-3-aminobenzene (coupler d) | 0.12 |
| Monoethanolamine | 4.28 |
| Mixture of linear $C_{18}$ to $C_{24}$ alcohols ($C_{18}/C_{20}/C_{22}/C_{24}/(7/58/30/6)$) | 4.6 |
| Carboxyvinyl polymer (Carbopol 980 from Lubrizol) | 0.1 |
| Glycerol | 5 |
| Oxyethylenated (10 OE) oleyl alcohol | 1 |
| Oxyethylenated (20 OE) oleyl alcohol | 4 |
| Oxyethylenated (5 OE) decyl alcohol | 1.2 |
| Oxyethylenated (60 OE) cetylstearyl ($C_{16}/C_{18}$) alcohol ether of myristyl glycol | 0.01 |
| Sequestrant | 0.2 |
| Reducing agent | 0.22 |
| Antioxidant | 0.12 |
| Deionized water | q.s. for 100 | b. Dyeing Composition A5:

| Composition | A5 |
| --- | --- |
| Liquid petroleum jelly (fatty substance a) | 50 |
| Cetylstearyl alcohol (50/50 $C_{16}/C_{18}$) (fatty substance a) | 2 |
| 2-(2,5-Diaminophenyl)ethanol sulfate (oxidation base c) | 1.58 |
| 6-Hydroxybenzomorpholine (coupler d) | 0.033 |
| 1-β-Hydroxyethyloxy-2,4-diaminobenzene dihydrochloride (coupler d) | 0.02 |
| 1,3-Dihydroxybenzene (resorcinol) (coupler d) | 0.67 |
| 1-Hydroxy-3-aminobenzene (coupler d) | 0.12 |
| Disodium ethylenediaminetetraacetate dihydrate | 0.2 |
| Monoethanolamine | 5.4 |
| Carboxyvinyl polymer (Carbopol 980 from Lubrizol) | 0.4 |
| Sodium cetostearyl sulfate (50/50 $C_{16}/C_{18}$) | 2 |
| Oxyethylenated (20 OE) stearyl alcohol | 2 |
| Oxyethylenated (4 OE) sorbitan monolaurate | 5 |
| Antioxidant | 0.3 |
| Deionized water | q.s. for 100 |

2.2 Oxidizing Composition B4:

| Composition | B4 |
| --- | --- |
| Hydrogen peroxide as an aqueous 50% solution (200 vol. aqueous hydrogen peroxide solution) (chemical oxidizing agent f) | 12 |
| Disodium tin hexahydroxide | 0.04 |
| Tetrasodium pyrophosphate decahydrate | 0.03 |
| Liquid petroleum jelly | 20 |
| Poly[(dimethyliminio)-1,3-propanediyl(dimethyliminio)-1,6-hexanediyl dichloride] as an aqueous 60% solution | 0.25 |
| Polydimethyldiallylammonium chloride at 40% in water, non-stabilized | 0.5 |
| Glycerol | 0.5 |
| Cetylstearyl alcohol (30/70 $C_{16}/C_{18}$) | 6 |
| Oxyethylenated (20 OE) stearyl alcohol | 5 |
| Protected oxyethylenated (4OE) rapeseed acid amide | 1.3 |
| Vitamin E: DL-α-Tocopherol | 0.1 |
| Sequestrant | 0.15 |
| Deionized water | q.s. for 100 |

2.3 Procedure

The dyeing compositions A4, A5 are mixed separately with the oxidizing composition B4, in proportions of one part of dyeing composition for one part of oxidizing composition.

The mixtures A4+B4, A5+B4 are then applied to locks of hair comprising 90% white hairs, in a proportion of 10 grams of mixture for one gram of lock.

After a leave-on time of 35 minutes at 27° C., the hair is rinsed with clear water and then a conditioning shampoo is applied to the hair.

After drying, a light chestnut-brown shade of good strength and coverage is obtained on the hair.

The invention claimed is:

1. A cosmetic composition comprising:
 a) at least one fatty substance;
 b) at least one polymer chosen from cellulose polymers and carboxylic anionic polymers;
 c) at least one oxidation base chosen from (2,5-diaminophenyl)ethanol, and the acid salts, solvates, and hydrates thereof;
 d) optionally at least one coupler;
 e) optionally at least one basifying agent; and
 f) at least one chemical oxidizing agent;
 wherein the cosmetic composition comprises a total fatty substance content of at least about 10% by weight, relative to the total weight of the cosmetic composition;
 wherein said cosmetic composition is prepared by mixing a composition (A) and a composition (B),
  wherein composition (A) comprises:
   c) the at least one oxidation base;
   d) optionally, the at least one coupler; and
   e) optionally, the at least one basifying agent; and
  wherein composition (B) comprises:
   f) the at least one chemical oxidizing agent; and
  wherein compositions (A) and (B) are mixed in a weight ratio of (A)/(B) ranging from 0.2 to 10.

2. A cosmetic composition according to claim 1, wherein the at least one fatty substance is chosen from $C_6$-$C_{16}$ hydrocarbons, hydrocarbons comprising more than 16 carbon atoms, non-silicone oils of animal origin, vegetable oils of triglyceride type, synthetic triglycerides, fluoro oils, fatty alcohols, esters of fatty acids and/or fatty alcohols other than triglycerides, plant waxes, non-silicone waxes, silicones, and mixtures thereof.

3. A cosmetic composition according to claim 1, wherein the at least one fatty substance is liquid at ambient temperature and at atmospheric pressure.

4. A cosmetic composition according to claim 1, wherein the at least one fatty substance is chosen from liquid petroleum jelly, polydecenes, liquid fatty alcohols, liquid esters of fatty acids and/or of fatty alcohols, and mixtures thereof.

5. A cosmetic composition according to claim 1, wherein the cosmetic composition comprises a total fatty substance content ranging from about 10% to about 80% by weight, relative to the total weight of the cosmetic composition.

6. A cosmetic composition according to claim 1, wherein the at least one polymer is chosen from associative polymers.

7. A cosmetic composition according to claim 1, wherein the at least one polymer is chosen from non-associative polymers.

8. A cosmetic composition according to claim 1, wherein the at least one polymer is chosen from cellulose ethers and hydroxyalkylcelluloses.

9. A cosmetic composition according to claim 1, wherein the at least one polymer is chosen from non-ionic, cationic, and anionic cellulose polymers.

10. A cosmetic composition according to claim 1, wherein the at least one polymer is chosen from anionic polymers comprising at least one optionally salified, unsaturated carboxylic acid monomer.

11. A cosmetic composition according to claim 1, wherein the carboxylic anionic polymers comprise at least one monomer chosen from acrylic acid and methacrylic acid monomers, which are optionally salified.

12. A cosmetic composition according to claim 1, wherein the carboxylic anionic polymers are associative and are chosen from the following polymers and salts thereof:
(A) polymers comprising at least one hydrophilic unit, and at least one fatty-chain allyl ether unit, wherein the hydrophilic unit comprises a vinylcarboxylic acid, and wherein the fatty-chain allyl ether unit is chosen from monomers of formula (A1) below:

$$H_2C=C(R')-CH_2-O-(B)_n-R \quad (A1)$$

wherein:
R' is chosen from H and $(C_1-C_6)$alkyl groups;
B is chosen from divalent radicals -(alk-O)—, wherein alk is chosen from linear or branched $(C_1-C_6)$alkylene groups;
n is zero or an integer ranging from 1 to 100;
R is a hydrocarbon-based radical chosen from alkyl, arylalkyl, aryl, alkylaryl, cycloalkyl, cycloalkylalkyl, and alkylcycloalkyl radicals comprising from 8 to 30 carbon atoms;
(B) maleic anhydride/$C_{30}$-$C_{38}$ α-olefin/alkyl maleate terpolymers;
(C) acrylic terpolymers comprising:
(i) from about 20% to about 70% by weight of an α,β-monoethylenically unsaturated carboxylic acid,
(ii) from about 20% to about 80% by weight of a non-surfactant α,β-monoethylenically unsaturated monomer other than (i), and
(iii) from about 0.5% to about 60% by weight of a non-ionic monourethane which is the product of reaction of a monohydric surfactant with a monoethylenically unsaturated monoisocyanate;
(D) copolymers comprising at least one monomer chosen from α,β-monoethylenically unsaturated carboxylic acids and esters of α,β-monoethylenically unsaturated carboxylic acids and of oxyalkylenated fatty alcohols; and
(E) copolymers comprising at least one hydrophilic unit of unsaturated olefinic carboxylic acid type and at least one hydrophobic unit of $C_{10}$-$C_{30}$ alkyl ester of unsaturated carboxylic acid type.

13. A cosmetic composition according to claim 1, wherein the carboxylic anionic polymers are non-associative and are chosen from homopolymers and copolymers of acrylic or methacrylic acid which are optionally crosslinked, and salts thereof.

14. A cosmetic composition according to claim 1, wherein the at least one polymer is present in the cosmetic composition in an amount ranging from about 0.05% to about 10% by weight, relative to the total weight of the cosmetic composition.

15. A cosmetic composition according to claim 1, wherein the at least one chemical oxidizing agent is hydrogen peroxide.

16. A cosmetic composition according to claim 1, further comprising at least one surfactant chosen from non-ionic surfactants, anionic surfactants, zwitterionic surfactants, and combinations thereof.

17. A cosmetic composition according to claim 16, wherein the at least one surfactant is present in the cosmetic composition in an amount ranging from about 0.1% to about 50% by weight, relative to the total weight of the cosmetic composition.

18. A cosmetic composition according to claim 1, wherein the at least one oxidation base is present in the cosmetic composition in an amount ranging from about 0.0001% to about 20% by weight, relative to the total weight of the cosmetic composition.

19. A cosmetic composition according to claim 1, wherein the at least one coupler is chosen from meta-phenylenediamines, meta-aminophenols, meta-diphenols, naphthalene-based couplers, heterocyclic couplers, and the addition salts thereof.

20. A cosmetic composition according to claim 1, wherein the at least one basifying agent is chosen from aqueous ammonia, alkali metal carbonates and bicarbonates, sodium hydroxide, potassium hydroxide, organic amines, amino acids in neutral or ionic form, compounds of formula (A11) below, and mixtures thereof:

wherein:
W is chosen from divalent $C_1$-$C_6$ alkylene radicals optionally substituted with at least one hydroxyl group or $C_1$-$C_6$ alkyl radical, and/or optionally interrupted with at least one heteroatom, and $NR_u$; and
$R_x$, $R_y$, $R_z$, $R_t$ and $R_u$, which may be identical or different, are chosen from hydrogen and $C_1$-$C_6$ alkyl, $C_1$-$C_6$ hydroxyalkyl, and $C_1$-$C_6$ aminoalkyl radicals.

21. A process for dyeing keratin fibers comprising applying to the keratin fibers a cosmetic composition comprising:
a) at least one fatty substance;
b) at least one polymer chosen from cellulose polymers and carboxylic anionic polymers;
c) at least one oxidation base chosen from (2,5-diaminophenyl)ethanol, and the acid salts, solvates, and hydrates thereof;
d) optionally at least one coupler;
e) optionally at least one basifying agent; and
f) at least one chemical oxidizing agent;
wherein said cosmetic composition is prepared by mixing a composition (A) and a composition (B), wherein composition (A) comprises:
c) the at least one oxidation base;
d) optionally, the at least one coupler; and
e) optionally, the at least one basifying agent; and wherein composition (B) comprises:
f) the at least one chemical oxidizing agent;

wherein compositions (A) and (B) are mixed in a weight ratio of (A)/(B) ranging from 0.2 to 1; and wherein the cosmetic composition comprises a total fatty substance content of at least about 10% by weight, relative to the total weight of the cosmetic composition.

22. A process according to claim 21, wherein composition (A) comprises:
at least one oxidation base c);
at least one coupler d);
optionally at least one basifying agent e); and wherein at least one of the compositions (A) and (B) comprises:
at least one fatty substance a), and
at least one polymer b).

23. A process according to claim 21, wherein the cosmetic composition results from the mixing of three compositions, wherein the three compositions are aqueous or wherein at least one of the three compositions is anhydrous.

24. A process according to claim 23, wherein of the cosmetic composition results from the mixing of two aqueous compositions A and B and an anhydrous composition (A'), wherein:
composition (A') comprises at least one fatty substance a),
composition A comprises at least one oxidation base c) and at least one coupler d);
composition B comprises at least one chemical oxidizing agent f);
compositions (A') and/or A optionally comprise at least one basifying agent e);
at least one of compositions (A'), A, or B comprise at least one polymer b); and
wherein the total fatty substance content of the cosmetic composition resulting from the mixing of the three compositions (A')+A+B is at least about 10% by weight, relative to the total weight of the cosmetic composition.

25. A multi-compartment device comprising:
either
i) a first compartment containing composition (A) comprising:
at least one oxidation base chosen from (2,5-diaminophenyl)ethanol, and the acid salts, solvates, and hydrates thereof c);
at least one coupler d);
optionally at least one basifying agent e); and
ii) at least a second compartment containing composition (B) comprising:
at least one chemical oxidizing agent f);
wherein at least one of the compositions (A) and (B) comprises:
at least one fatty substance a), and
at least one polymer b); and,
wherein a cosmetic composition resulting from mixing compositions (A)+(B) comprises a total fatty substance content of at least about 10% by weight, relative to the total weight of the cosmetic composition resulting from the mixing of (A)+(B);
or
i) a first compartment containing an anhydrous composition (A') comprising at least one fatty substance a);
ii) a second compartment containing a cosmetic composition A comprising at least one oxidation base c) and at least one coupler d); and
iii) at least a third compartment containing composition B comprising at least one chemical oxidizing agent f); wherein a cosmetic composition resulting from the mixing of (A')+A+B comprises a total fatty substance content of at least about 10% by weight, relative to the total weight of the cosmetic composition resulting from the mixing of (A')+A+B.

* * * * *